United States Patent [19]

Leibfried, Sr.

[11] Patent Number: 5,013,809

[45] Date of Patent: * May 7, 1991

[54] ORGANOSILICON COMPOSITIONS

[75] Inventor: Raymond T. Leibfried, Sr., Wilmington, Del.

[73] Assignee: Hercules Incorporated, Wilmington, Del.

[*] Notice: The portion of the term of this patent subsequent to Feb. 12, 2007 has been disclaimed.

[21] Appl. No.: 419,429

[22] Filed: Oct. 10, 1989

Related U.S. Application Data

[63] Continuation-in-part of Ser. No. 79,740, Jul. 30, 1987, Pat. No. 4,900,779, which is a continuation-in-part of Ser. No. 901,092, Aug. 27, 1986, abandoned.

[51] Int. Cl.$^5$ .............................................. C08L 83/04
[52] U.S. Cl. .................................... 524/862; 523/222; 525/479; 528/15; 528/31; 528/25; 556/460; 556/462; 556/479; 264/328.18; 264/331.13; 264/331.17
[58] Field of Search ...................... 264/328.18, 331.11, 264/331.13, 331.1; 524/862; 523/222; 525/479; 528/15.31, 25; 556/460, 462, 479

[56] References Cited

U.S. PATENT DOCUMENTS

| | | | |
|---|---|---|---|
| 2,624,721 | 1/1953 | Hatcher | 260/46.5 |
| 2,624,721 | 1/1953 | Hatcher | 260/46.5 |
| 2,665,287 | 1/1954 | Hatcher | 260/448.2 |
| 2,823,218 | 2/1958 | Speier | 260/448.2 |
| 3,197,432 | 7/1965 | Lamoreaux | 260/46.5 |
| 3,197,433 | 7/1965 | Lamoreaux | 260/46.5 |
| 3,198,766 | 8/1965 | Nitzsche et al. | 260/46.5 |
| 3,220,972 | 11/1965 | Lamoreaux | 260/46.5 |
| 3,929,850 | 12/1975 | Streck et al. | 260/448.2 |
| 4,011,247 | 3/1977 | Sato et al. | 260/348 |
| 4,599,440 | 7/1986 | Watanabe | 556/460 |
| 4,639,501 | 1/1987 | Seyferth et al. | 528/15 |
| 4,719,273 | 1/1988 | Seyferth et al. | 528/15 |
| 4,877,820 | 10/1989 | Cowan | 523/222 |
| 4,900,779 | 2/1990 | Leibfried | 524/862 |
| 4,902,731 | 2/1990 | Leibfried | 524/862 |

FOREIGN PATENT DOCUMENTS

| | | |
|---|---|---|
| 0204171 | 12/1986 | European Pat. Off. . |
| 0204171 | 12/1986 | European Pat. Off. . |
| 2595363 | 3/1987 | France . |
| 2595364 | 3/1987 | France . |
| 767112 | 9/1980 | U.S.S.R. . |
| 1439945 | 6/1976 | United Kingdom . |

OTHER PUBLICATIONS

Risse et al., "Di-and Tetrafunctional Initiators for the Living Ring-Opening Olefin Metathesis Polymerization of Strained Cyclic Olefins" (1989).

Nogaideli et al., "Hydroxylation of dicyclopentadiene With Organochlorosilanes and Siloxanes", Soobschh. Akad. Nauk Gruz. SSR. 82. No. 3 589 (1976).

Kim et al., "Polycycloalkylene-Siloxane Polymers: Synthesis and Thermal Study", 16 *Journal of Polymer Science: Polymer Chemistry* Edition, 483-490 (1978).

*Primary Examiner*—Melvyn I. Marquis
*Attorney, Agent, or Firm*—Mark D. Kuller

[57] ABSTRACT

Organosilicon prepolymer compositions which are the reaction products of (a) at least one of cyclic polysiloxanes or tetrahedral siloxysilanes containing at least two ≡SiH groups and (b) polycyclic polyenes having at least two non-aromatic, non-conjugated carbon-carbon double bonds in their rings, wherein the total ratio of the non-aromatic, non-conjugated carbon-carbon double bonds in the rings of (b) to ≡SiH groups in (a) in greater than 1.8:1 and either the ≡SiH containing compounds (a) or the polycyclic polyenes (b) have more than two reactive sites. The organosilicon compositions are blended with (c) at least one of additional cyclic polysiloxanes, additional tetrahedral siloxysilanes or linear, short chain ≡SiH terminated polysiloxanes to make fluid hydrosilation compositions. These storable blends are polymerized to thermally stable thermoset polymers.

24 Claims, No Drawings

ORGANOSILICON COMPOSITIONS

This is a continuation-in-part of U.S. patent application Ser. No. 07/079,740, filed Jul. 30, 1987, now U.S. Pat. No. 4,900,799, which is a continuation-in-part of U.S. patent application Ser. No. 06/901,092, filed Aug. 27, 1986, now abandoned.

This invention relates to a new and novel class of organosilicon prepolymer compositions useful for making thermoset organosilicon polymers, the process of making such compositions, blends of such prepolymers with ≡SiH bearing polysiloxanes or siloxysilanes useful for making thermoset organosilicon polymers, the processes of making the prepolymers and blends, and the processes of preparing polymers from such blends.

BACKGROUND OF THE INVENTION

A new class of high molecular weight organosilicon polymers which have excellent physical, thermal and electrical properties and outstanding resistance to water, and that can be used to prepare shaped articles is described in parent applications Ser. Nos. 07/079,740 and 06/901,092. They are thermoset or thermoplastic organosilicon polymers comprising alternating polycyclic hydrocarbon residues and cyclic polysiloxanes or tetrahedral siloxysilane residues linked through carbon to silicon bonds. This application is directed to novel organosilicon prepolymer compositions that can be used to prepare such polymers, blends of such prepolymers with ≡SiH bearing polysiloxanes and siloxysilanes useful for making thermoset organosilicon polymers, the processes of making the prepolymers and the blends, and the processes of preparing thermoset organosilicon polymers from such blends.

SUMMARY OF THE INVENTION

The novel organosilicon prepolymer compositions of this invention are the reaction products of (a) at least one of cyclic polysiloxanes or tetrahedral siloxysilanes containing at least two ≡SiH groups and (b) polycyclic polyenes having at least two non aromatic, non conjugated carbon-carbon double bonds in their rings, wherein the total ratio of the non aromatic, non-conjugated carbon-carbon double bonds in the rings of (b) to ≡SiH groups in (a) is greater than 1.8:1 and either the ≡SiH containing compounds (a) or the polycyclic polyenes (b) have more than two reactive sites. In addition, this invention is directed to a process for forming such organosilicon compositions comprising reacting, in the presence of a hydrosilation catalyst, (a) cyclic polysiloxanes or tetrahedral siloxysilanes containing at least two ≡SiH groups and (b) polycyclic polyenes having at least two non aromatic, non-conjugated carbon-carbon double bonds in their rings, wherein the ratio of the non-aromatic, non-conjugated carbon-carbon double bonds in the rings of (b) to ≡SiH groups in (a) is at least 1.8:1 and at least one of the compounds (a) and (b) has more than two reactive sites. The invention is further directed to a low viscosity fluid blend of the organosilicon prepolymer composition with (c) at least one of additional cyclic polysiloxanes, additional tetrahedral siloxysilanes or linear, short chain ≡SiH terminated polysiloxanes such that the total ratio of the non aromatic, non-conjugated carbon-carbon double bonds in the rings of (b) (used to form the organosilicon prepolymer composition) to ≡SiH groups in (a) and (c) (the total ≡SiH groups of the cyclic polysiloxanes, tetrahedral siloxysilanes and linear, short chain ≡SiH terminated polysiloxanes used to form the organosilicon prepolymer composition and added to form the blend) is in the ratio of 0.4:1 to 1.7:1, the process of forming such blends by mixing the components, and a process for forming thermoset organosilicon polymers by curing such blends in the presence of a hydrosilation catalyst.

DETAILED DESCRIPTION OF THE INVENTION

Any cyclic polysiloxane or tetrahedral siloxysilane with two or more hydrogen atoms bound to silicon will enter into the reaction. Cyclic polysiloxanes useful in forming the products of this invention have the general formula:

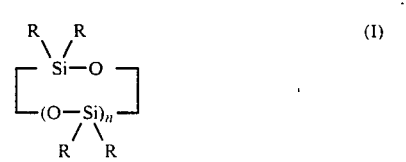

wherein R is hydrogen or a substituted or unsubstituted alkyl, alkoxy, aromatic or aryloxy radical, n is an integer from 3 to about 20, and R is hydrogen on at least two of the silicon atoms in the molecule.

The tetrahedral siloxysilanes are represented by the general structural formula:

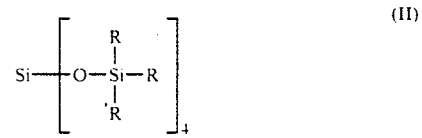

wherein R is as defined above and is hydrogen on at least two of the silicon atoms in the molecule.

Examples of reactants of Formula (I) include, e.g., tetramethylcyclotetrasiloxane, pentamethylcyclopentasiloxane, hexamethylcyclohexasiloxane, tetraethylcyclotetrasiloxane, cyclotetrasiloxane, tetraphenylcyclotetrasiloxane, tetraoctylcyclotetrasiloxane and hexamethyltetracyclosiloxane.

The most commonly occurring members of this group are the tetra- , penta- and hexamethylcyclotetrasiloxane, with tetramethylcyclotetrasiloxane being a preferred member. In most cases, however, the material is a mixture of a number of species wherein n can vary widely. Generally, commercial mixtures contain up to about 20% (in purer forms as low as 2%) low molecular weight linear methylhydrosiloxanes, such as heptamethyltrisiloxane, octamethyltetrasiloxane, etc.

Examples of reactants of Formula (II) include, e.g., tetrakisdimethylsiloxysilane, tetrakisdiphenylsiloxysilane, and tetrakisdiethylsiloxysilane. The tetrakisdimethylsiloxysilane is the best known and preferred species in this group.

Polycyclic polyenes which can be employed are polycyclic hydrocarbon compounds having at least two non-aromatic, non-conjugated carbon-carbon double bonds in their rings. Illustrative are compounds selected from the group consisting of cyclopentadiene oligomers (e.g., dicyclopentadiene, tricyclopentadiene and tetracyclopentadiene), bicycloheptadiene and its diels-alder oligomers with cyclopentadiene (e.g., dimethanohexahydronaphthalene), and substituted derivatives of any of these, e.g., methyl dicyclopentadiene. Preferred are bicycloheptadiene, dimethanohexahydronaphthalene, dicyclopentadiene and tricyclopentadiene, with the most preferred being bicycloheptadiene. Two or more polycyclic polyenes can be used in combination.

The linear, short chain ≡SiH terminated polysiloxanes preferably have the general formula:

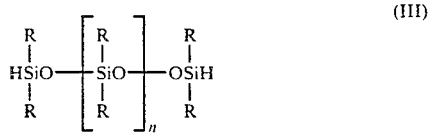

(III)

wherein n is 0 to 1000 and R is alkyl or aryl, preferably methyl or phenyl. Such polysiloxanes may be added by themselves or with cyclic siloxanes or tetrahedral siloxysilanes. In such combinations, they preferably are used in an amount 10 to 50%, by weight of the polysiloxanes and siloxysilanes added to the preformed olefin reaction product. These polysiloxanes impart flexibility to the cured polymers and can be used to produce elastomers.

The reactions for forming the organosilicon prepolymer composition and for forming crosslinked polymers from the organosilicon prepolymer composition can be promoted thermally or by the addition of a hydrosilation catalyst or radical generators such as peroxides and azo compounds. Hydrosilation catalysts include metal salts and complexes of Group VIII elements. The preferred hydrosilation catalysts contain platinum.

The reactions for forming the organosilicon prepolymer compositions and crosslinked polymer proceed readily in the presence of a platinum containing catalyst. The preferred catalyst, in terms of both reactivity and cost, is chloroplatinic acid ($H_2PtCl_6 \cdot 6H_2O$) Catalyst concentrations of 0.0005 to about 0.05% by weight, based on weight of the reactants, will effect smooth and substantially complete polymerization. Other platinum compounds can also be used to advantage in some instances, such as $PtCl_2$ and dibenzonitrile platinum dichloride. Platinum on carbon is also effective for carrying out high temperature polymerizations. Other useful platinum catalysts are disclosed in, e.g., U.S. Pat. Nos. 3,220,972, 3,715,334 and 3,159,662. An exhaustive discussion of the catalysis of hydrosilation can be found in Advances in Organometallic Chemistry, Vol. 17, beginning on page 407.

It is possible, by selection of reactants, reactant concentrations and reaction conditions, to prepare prepolymers and polymers exhibiting a broad range of properties and physical forms. Thus, it has been found possible to prepare prepolymer liquids, elastomeric materials and glassy polymers.

The organosilicon prepolymer compositions are made with a large excess of carbon-carbon double bonds available for reaction with ≡SiH groups. That is, the ratio of reactants is such that the ratio of the non-aromatic, non-conjugated carbon-carbon double bonds in the rings of (b) to ≡SiH groups in (a) is greater than 1.8:1, preferably greater than 1.8:1 and up to 5:1, and most preferably greater than 1.8:1 and up to 2.2:1.

The organosilicon prepolymer compositions of this invention may be prepared by mixing the reactants and the platinum catalyst and bringing the mixture to a temperature at which the reaction is initiated and proper temperature conditions are thereafter maintained to drive the reaction to substantial completion (typically, due to the large ratio of double bonds to ≡SiH groups available for reaction greater than 90% of the ≡SiH are consumed).

The prepolymer compositions are generally in the form of a flowable liquid, which is stable at room temperature. At a 2:1 double bond to ≡SiH ratio it is assumed that stoichiometrically all ≡SiH bonds are reacted with carbon-carbon double bonds and that the prepolymer is stable against further reaction. Prepolymers having such a stoichiometric ratio are the most stable prepolymers of this invention. Also, due to their odor, the presence of unreacted polycyclic polyenes is undesirable. If unreacted polycyclic polyenes are present, they can be stripped, e.g., using a rotoevaporator, to form odorless compositions.

The basic reaction is fast. However, it is exothermic, and without using heat removal equipment (cooling coils or reflux condenser) the prepolymer must be formed slowly (up to twenty-four hours, depending on the reaction mass). In a continuous process with adequate heat removal the reaction be carried out quickly. When 90% or more of the ≡SiH groups are reacted the prepolymers are stable indefinitely at room temperature.

The crosslinked polymers ar formed by mixing the prepolymer compositions of this invention with (c) at least one of additional cyclic polysiloxanes, additional tetrahedral siloxysilanes or linear, short chain ≡SiH terminated polysiloxanes such that the total ratio of non-aromatic, non-conjugated carbon-carbon double bonds in the rings of (b) to ≡SiH groups in (a) and (c) is in the ratio of 0.4:1 to 1.7:1; preferably 0.8:1 to 1.3:1, most preferably about 1:1, to form a low viscosity solution, and curing the mixture in the presence of a hydrosilation catalyst.

In a preferred embodiment, the organosilicon prepolymer composition is reacted with the polysiloxanes and/or tetrahedral siloxysilanes to form a crosslinked polymer in a mold. The prepolymer composition and polysiloxanes/ siloxysilanes are stored separately and are blended in an in-line mixer directly before entering the mold. The hydrosilation catalyst may be present in either stream or injected directly into the mixer. The reaction is exothermic and proceeds rapidly so that the polymer gels and the product can be removed from the mold in minutes.

The components of the blends are completely stable until they are mixed. This permits indefinite room temperature storage of the materials. If the reaction upon mixing is too fast and viscosity increases rapidly preventing proper mold filling, a cure rate retardant (e.g. tetramethylethylenediamine) can be added.

Alternately, the blend components of this invention can be premixed and stirred in a tank. These blends have low viscosity and are pumpable. Addition of catalyst and/or application of heat can be used to cure the prepolymer composition. The reaction can be carried out in an extruder, mold or oven, or the blend can be is applied directly on a substrate or part. For the more reactive compositions, mild complexing agents, such as tetramethylethylenediamine, can be added to control the room temperature reaction. The complex disassociates at temperatures greater than 100° C. to let curing proceed. With stronger complexing agents, such as phosphorus compounds, curing temperatures above 150° C. are required.

Although a hydrosilation reaction via the carbon-carbon unsaturation of the polycyclic polyene rings and the ≡SiH group is the primary polymerization and crosslinking mechanism, other types of polymerization and crosslinking may also take place as the curing temperature is increased. These may include, e.g., oxidative crosslinking, free radical polymerization (olefin addition reactions) and condensation of ≡SiH with silanols to form siloxane bonds.

Additives such as fillers and pigments are readily incorporated. Carbon black, vermiculite, mica, wollastonite, calcium carbonate, sand, glass spheres, glass beads, ground glass and waste glass are examples of fillers which can be incorporated. Fillers can serve either as reinforcement or as fillers and extenders to reduce the cost of the molded product. Glass spheres are especially useful for preparing low density composites. When used, fillers can be present in amounts up to about 80%. Stabilizers and antioxidants are useful to maintain storage stability of the formulations and thermal oxidative stability of the final product. Coupling agents such as vinyl silane and related compounds may be used to wet the glass and promote adhesion of the resin to the glass.

For instance, chopped glass fibers can be slurried in a stabilized liquid blend (prepolymer and added siloxane or siloxysilane) in compounding equipment having a blade stirrer(s) or screw mixer(s). It is best to deaerate such a slurry under vacuum before injecting it into a mold.

Glass or carbon, e.g., graphite, fibers are wetted very well by the liquid blends, making the blends excellent matrix materials for high strength composite structures. Thus, the prepolymer composition can be mixed with cyclic siloxanes, tetrahedral siloxanes and/or linear, short chain ≡SiH terminated polysiloxanes to form a blend, and a mold containing the requisite staple or continuous filament can be charged with the blend, and the blend can be cured to form the desired composite structure. Fiber in fabric form can also be employed. Fiber reinforced composites of the polymers of this invention can contain as much as 80%, preferably 30 to 60%, by weight, of fibrous reinforcement, and, when fully cured, typically exhibit extremely high tensile and flexural properties and also excellent impact strength. Other types of fibers, e.g., metallic, ceramic and synthetic polymer fibers, also work well.

The low-viscosity fluid blends are well suited for use in reactive molding systems, where rapid mixing and flow into a mold is important. The low viscosity and affinity for glass permits filling of molds containing glass reinforcement. The high reactivity of the blends gives a fast gel time at reasonable temperatures so that molded parts can be quickly taken out of the mold and cured further outside the mold.

The thermoset polymers fabricated from the prepolymer compositions and blends described herein are useful in molded electronic parts, electrical connectors, electronic and electrical part encapsulation, and various aerospace applications. They can be molded into highly reinforced, intricate shapes and their inherent high thermal stability, low moisture absorbance and fire resistance (high char yield at 1000° C. in air) make them uniquely suitable for such uses.

The thermoset polymers are also useful as structural adhesives, curable in situ, to form strong bonds due to a high affinity of ≡SiH derived silanol groups for polar metal surfaces, especially oxidized metal surfaces. The elastomeric embodiments make excellent potting compounds for electronic applications since they can be cured in situ and have a low equilibrium water content (0.01-0.1%) after humid aging (100% relative humidity (RH), 1 week).

The glass filled, thermoset products which have been polymerized to the glassy state are characterized by high physical properties, i.e., high modulus and high tensile strength and good flex properties. They are fire resistant, burn very slowly when subjected to a flame, and self-extinguish when the flame is removed.

Thermal properties of the thermoset polymers are outstanding. The glass transition temperature (Tg) of a fully cured thermoset polymer is about 200° C. or higher. Thermal stability is excellent with usually less than 10% weight loss at 500° C. during Thermogravimetric analysis. At 1000° C. in air, they leave about 50% of a ceramic residue. This high temperature resistance makes them useful as refractory materials, fire resistant materials and ablative materials.

The thermoset polymers are also resistant to oxidation at ordinary temperatures. Above 200° C., oxidative crosslinking of silicon portions of the molecule appears to take place, resulting in the formation of a dark siliceous outer layer. This oxidized outer layer appears to impede the oxidative degradation of the bulk polymer.

The following examples are presented to demonstrate this invention. They are not intended to be limiting. Therein, all percentages, parts, etc., are by weight, unless otherwise indicated.

EXAMPLE 1

This example shows preparation of an organosilicon prepolymer composition of this invention.

With continuous mixing, 0.031 part bisbenzonitrile platinum dichloride, 120.4 parts (2.0 mole, 4.0 equivalents (eq)) bicycloheptadiene, and 120.4 parts (0.05 mole, 2.0 eq) methylhydrocyclosiloxanes (a mixture of tetramethylcyclotetrasiloxane, pentamethylcyclotetrasiloxane, hexamethylcyclotetrasiloxane, available from Huls/Petrarch, Bristol, Pa.) were added to a reaction chamber and heated gradually to 100° C. over a period of seven hours and held at 100° C. for ten hours. A yield of 298.5 parts (98%) was obtained.

IR analysis was conducted and the product was found not to have a peak at 2140 cm$^{-1}$ (SiH peak), indicating that the hydrosilation reaction was complete.

Proton NMR analysis showed that SiH and bicycloheptadiene double bonds had reacted and the expected Si-C bonds had formed (5.8-6.0 ppm) giving bicycloheptene substituted methylhydrocyclosiloxane as a pourable fluid.

EXAMPLE 2

This example shows preparation of a thermoset polymer using the prepolymer composition prepared in Example 1.

A clear solution was prepared by stirring 110 parts of the prepolymer composition prepared in Example 1 with 48 parts (80 milliequivalents (meq)) of methylhydrocyclosiloxanes. The resultant low viscosity mixture was poured into a slotted mold (3 inch × ¼ inch × ⅛ inch) and the mold was put under full vacuum for 5 minutes to remove entrained air. The mold was heated to 100° C. for 10 hours and a hard polymer was produced. After further curing (150° C./4 hours, 225° C./2 hours and 285° C./4 hours) the polymer was evaluated using thermogravimetric analysis. It was stable in air and nitrogen to 475° C., and the residue at 1000° C. was 60.75% in nitrogen (50.42% in air).

momechanical Analyzer with a 100 mg load, and expansion probe at 10° C./minute.

TABLE 1

| | | THERMOGRAVIMETRIC ANALYSIS | | | | | |
|---|---|---|---|---|---|---|---|
| | | Air | | | Nitrogen Atmosphere | | |
| Sample | Max Cure (°C.) | Weight loss (°C.) | Break (°C.)[1] | Residue (% @ 1000° C.) | Weight loss (°C.) | Break (°C.)[1] | Residue (% @ 1000° C.) |
| Example 3 | 150 | 240–350 (6%) | 440 | 52.59 | 240–350 (8%) | 475 | 62.75 |
| Example 3 | 285 | — | 470 | 59.25 | — | 470 | 60.03 |
| Example 4 | 225 | 300–390 (3%) | 480 | 54.09 | 280–350 (2%) | 470 | 60.40 |

[1]Break is the point at which the sample has lost 10 weight percent of its original weight.

EXAMPLE 3

This example shows preparation of a glass cloth reinforced composite using the prepolymer composition Prepared in Example 1.

A clear solution was prepared by stirring 110 parts of the prepolymer composition prepared in Example 1 with 48.3 parts (72 meq) of methylhydrocyclosiloxanes. The fluid was injected into two warm (~100° C.) dry molds (5 inch×5 inch×⅛ inch) containing 52 parts of unsized fiberglass cloth. An increase in temperature indicated that the resin was polymerizing to a solid in the warm molds after 10 minutes. The above was cured for 10 hours at 100° C. and a hard polymer was produced. After further curing at 150° C./4 hrs., 225° C./2 hrs., and, then, 285° C./4 hrs., the composites were analyzed as described below.

EXAMPLE 4

This example shows preparation of a thermoset polymer using the prepolymer composition prepared in Example 1.

A clear solution was prepared as in Example 3 and poured into a three slotted, preheated mold (3 inch×½ inch×⅛ inch). The molds were maintained at 100° C. for 10 hours. Then, they were cured at 150° C. for 4 hours and 225° C. for 2 hours.

The following tests were carried out to determine the physical characteristics of the glass reinforced composite materials of Example 3 and the thermoset polymers of Example 4.

Dynamic modulus was measured in a Rheometrics Dynamic Spectrometer Model 7700 (Rheometrics, Inc., Piscataway, N.J.). A temperature sweep was carried out at a fixed frequency of 10 radians/second.

Flexural properties were measured in a standard Instron Universal Tester according to ASTM Method D790.

Thermogravimetric analysis was carried out in a Du Pont Thermal Analyzer (E. I. du Pont de Nemours & Company, Inc., Wilmington, Del.) at 20° C./minute.

Thermal Mechanical Analysis and Thermal Expansion Coefficient were measured using a Du Pont Ther-

TABLE 2

| | MODULUS (G') AND GLASS TRANSITION (Tg) DETERMINATIONS | | | |
|---|---|---|---|---|
| Sample | Max Cure (°C.) | G' 25° C. (dyne/cm²) | TΔG' (°C.) | Tg (°C. Tan max) |
| Example 3 (Glass Cloth Filled) | 150 | 1.9 × 10¹⁰ | 100 | 150 |
| Example 3 (Glass Cloth Filled) | 285 | 1.7 × 10¹⁰ | 220 | 300° C. |
| Example 4 (Unfilled) | 225 | 7.0 × 10⁹ | 110 | 142 |

TABLE 3

| | FLEXURAL STRENGTH AND MODULUS | | | |
|---|---|---|---|---|
| Designation | Max Cure (°C.) | Flexural Strength (psi[1]) | Flexural Modulus (ksi[2]) | Strain (%) |
| Example 3 (Glass Filled) | 150 | 6140 | 262 | 2.57 |
| Example 3 (Glass Filled) | 285 | 35800 | 2310 | 1.85 |
| Example 4 (Unfilled) | 225 | 7070 | 211 | 4.40 |

[1]Pounds per square inch.
[2]Thousands of pounds per per square inch.

EXAMPLE 5

This example shows preparation of an organosilicon prepolymer composition.

Into a reactor containing methylhydrocyclosiloxanes (mixture primarily comprised of tetramethylcyclotetrasiloxane, pentamethylcyclotetrasiloxane and hexamethylcyclotetrasiloxane available from Huls Petrarch) (25 parts), was added a solution of dicyclopentadiene and tricyclopentadiene (63.75 parts, 35.9 weight % tricyclopentadiene), chloroplatinic acid catalyst (in isopropyl alcohol) (35 parts per million (ppm)), and toluene (22.19 parts) over one hour. The exothermic reaction was controlled by the rate of addition and temperatures ranged from 78°–106° C. After addition was completed, 80% of the available ≡SiH groups had reacted. The mixture was stirred for 3.5 hours at 70° C. and found to have 87% of the ≡SiH groups reacted. Then, 35 ppm catalyst was added and after 3.5 hours of mixing at 70° C. the mixture was found to have 92% of the ≡SiH groups reacted. Heating for 15 hours at 70° C. brought the total ≡SiH reacted to 95%. Addition of 35 ppm catalyst and 8 hours heating at 70° C. brought the reaction to completion.

EXAMPLE 6

This example shows preparation of an organosilicon polymer using the organosilicon prepolymer composition of Example 1.

The bicycloheptadiene/methylhydrocyclosiloxanes prepolymer of Example 1 (5.1 parts) was stirred with hexamethyltrisiloxane (≡SiH terminated) (3.5 parts). Then, platinum catalyst (0.01 parts) was added with stirring. The mixture was deaerated under vacuum and poured into a slotted mold (3×½×⅛ inches), and cured at 120° C. for 2 hours and 150° C. for six hours. The cured polymer had a glass transition at 39° C. determined by differential scanning calorimetry. Thermogravimetric analysis indicated a 10% loss in weight at 500° C. in air and nitrogen, demonstrating the excellent stability of the polymer at high temperatures.

EXAMPLE 7

This example shows preparation of an organosilicon polymer.

The bicycloheptadiene/methylhydrocyclocsiloxanes prepolymer (5.1 parts) of Example 1 was stirred with ≡SiH terminated polydimethylsiloxane (Huls/Petrarch PS-537) (12.0 parts). Then, platinum catalyst (0.01 parts) was added with stirring. The compatible mixture was deaerated and poured into a slotted mold (3×½×⅛ inches) and cured at 120° C. for 2 hours and 150° C. for six hours. The cured polymer had a glass transition at −34° C. determined by differential scanning calorimetry. Thermogravimetric analysis indicated a 10% loss in the cured polymer at 500° C. in nitrogen and 490° C. in air, demonstrating the excellent stability of the polymer at high temperatures.

EXAMPLE 8

This example shows preparation of an organosilicon prepolymer composition.

Methylhydrocyclosiloxanes (0.75 eq SiH) (45.10 parts) and toluene (34.25 parts) were charged to a reaction chamber and stirred while dicyclopentadiene containing chloroplatinic acid complex was added at 45°-65° C. (74.37 parts) (1.13 eq olefin). The addition was carried out over 109 minutes and a cooling bath was used to control the exotherm. Bicycloheptadiene (17.28 parts (0.38 eq olefin)) was added over a period of one hour. An additional portion of a chloroplatinic acid catalyst complex with dimethenohexahydronaphthalene was added gradually over four days heating at 71°-73° C. to give 222 ppm pt in the product. Proton NMR analysis showed that the resin contained only 5.7% of the SiH originally charged.

EXAMPLE 9

This example shows preparation of an organosilicon polymer using the prepolymer composition of Example 8.

The prepolymer prepared in Example 8 (19.1 parts) was warmed to 50° C. and blended with methylhydrocyclosiloxanes (7.0 parts) containing tetramethylethylenediamine (50 ppm). The viscosity of the blend was 620 centistokes. The blend was poured into a finger mold and cured at 150° C. for 6 hours. Thermogravimetric analysis determined a 10% weight loss in the cured polymer at 540° C. in nitrogen and at 510° C. in air (20° C./min). The sample residue at 1000° C. was 66.1% in nitrogen and 48.1% in air.

EXAMPLE 10

This example shows preparation of a prepolymer composition.

A mixture of dicyclopentadiene (DCPD)/tricyclopentadiene (TCPD) (64.1% DCPD/35.9% TCPD) (63.75 parts) and chloroplatinic acid catalyst in isopropanol (35 ppm pt in resin) (0.12 parts chloroplatinic acid, 1.89 parts isopropanol) were dissolved in toluene (22.2 parts) and heated to 50° C. for one hour. This solution was added dropwise to methylhydrocyclosiloxanes (25 parts) stirring in a vessel under nitrogen. The addition was carried out over a period of one hour in a reaction temperature range of 74°-106° C. The addition rate was used to control the exotherm of the reaction. After an additional 5.5 hours with stirring at 70° C., 87% of the ≡SiH groups in the methylhydrocyclosiloxanes had reacted. Additional catalyst was added to give a total of 70 ppm pt in the resin prepolymer. After heating at 70° C. for 3.5 hours the ≡SiH groups were 92% reacted. Further heating a 70° C. (16 hours) brought the level of ≡SiH groups reacted to 95%.

EXAMPLE 11

This example shows preparation of an organosilicon polymer from the prepolymer composition of Example 10.

The prepolymer of Example 10 (17.17 parts) was stirred with methylhydrocyclosiloxanes (4.43 parts) containing 50 ppm tetramethylethylenediamine and toluene (17.34 parts). The resulting solution was coated on glass and cured at 120° C. for 1 hour and 150° C. for 6 hours. The cured polymer had a 10% weight loss at 500° C. in air and 500° C. in nitrogen, demonstrating the excellent thermal and thermal oxidative stability of the cured formulation.

EXAMPLE 12

This example shows preparation of an organosilicon polymer from the prepolymer composition of Example 1.

The bicycloheptadiene/methylhydrocyclosiloxanes prepolymer composition of Example 1 (15.00 parts) was stirred with tetramethyldisiloxane (6.61 parts). The compatible mixture was a fluid which was degassed under aspirator vacuum and poured into a slotted mold (3×½×⅛ inches) and cured at 50° C. for 2 hours, 120° C. for 2 hours and 150° C. for 6 hours. The cured polymer had 10% weight loss at 480° C. in nitrogen and 475° C. in air, showing excellent thermal and thermal oxidative stability. The polymer was cured further at 200° C. for 2 hours and 250° C. for 2 hours. The glass transition temperature of the cured polymer was 79° C. determined by thermal mechanical analysis. This corresponded closely with the temperature where the complex modulus (G′) decreased at the glass transition (80° C.) determined by dynamic mechanical analysis.

EXAMPLE 13

This example shows preparation of polymers from the prepolymer composition of Example 8 using various amounts of cyclic polysiloxane.

The prepolymer composition of Example 8 was stirred in toluene with various levels of methylhydrocyclosiloxanes to give a total olefin/≡SiH equivalent ratio ranging from 0.50/1.00 to 1.50/1.00. Total olefin includes the dicyclopentadiene and bicycloheptadiene olefin used to prepare the prepolymer before blending with methylhydrocyclosiloxanes (MHCS). Total ≡SiH includes ≡SiH in MHCS used to make the prepolymer (DCPD/BCHD/MHCS) before blending with MHCS and the MHCS added to make the coatings. The prepolymer was dissolved in toluene and MHCS was added before casting the coating on a glass plate with a 30 mil draw blade.

TABLE 4

| Prepolymer/ MHCS/Toluene (parts) | C=C:≡SiH* | Thermogravimetric Analysis 10% Weight Loss Temperature | | | |
|---|---|---|---|---|---|
| | | Air | Residue at 1000° C. | $N_2$ | Residue at 1000° C. |
| 3.06/3.00/1.50 | 0.5:1.0 | 500 | 58.0 | 525 | 71.5 |
| 4.60/3.00/3.20 | 0.67:1.0 | 410 | 54.8 | 520 | 64.0 |
| 9.20/3.00/3.50 | 1.0:1.0 | 500 | 48.2 | 520 | 65.7 |
| 9.40/1.50/3.00 | 1.35:1.0 | 500 | 37.9 | 510 | 58.1 |
| 11.04/1.20 | 1.5:1.0 | 500 | 31.9 | 500 | 48.8 |

*Total ratio of carbon-carbon double bonds in DCPD and BCPD used to form the prepolymers and ≡SiH groups in the MHCS used to form the prepolymer composition and polymer.

Excellent thermal and thermal oxidative stability is shown by the high temperatures required to give 10% weight loss. The high residues at 1000° C. indicate a high ceramic yield, which decreases as the amount of hydrocarbon in the formulation is increased.

While the invention has been described with respect to specific embodiments, it should be understood that they are not intended to be limiting and that many variations and modifications are possible without departing from the scope and spirit of this invention.

I claim:

1. An organosilicon prepolymer composition which is the reaction product of (a) at least one cyclic polysiloxane or tetrahedral siloxysilane containing at least two ≡SiH groups and (b) at least one polycyclic polyene having at least two non-aromatic, non-conjugated carbon-carbon double bonds in its rings, wherein the total ratio of the non-aromatic, non-conjugated carbon-carbon double bonds in the rings of (b) to ≡SiH groups in (a) is greater than 1.8:1 and either (a) or (b) has more than two reactive sites.

2. An organosilicon prepolymer composition as claimed in claim 1 wherein (a) is at least one cyclic polysiloxane having the general formula:

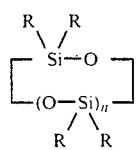   (I)

wherein R is hydrogen or a substituted or unsubstituted alkyl, alkoxy, aromatic or aryloxy radical, n is an integer from 3 to about 20, and R is hydrogen on at least two of the silicon atoms in the molecule; or at least one tetrahedral siloxysilane having the general structural formula:

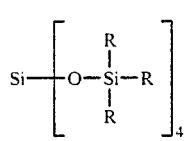   (II)

wherein R is as defined above and is hydrogen on at least two of the silicon atoms in the molecule.

3. An organosilicon prepolymer composition as claimed in claim 1 wherein the polycyclic polyene is selected from the group consisting of cyclopentadiene oligomers, dimenthano-hexahydronaphthalene, and substituted derivatives thereof.

4. An organosilicon prepolymer composition as claimed in claim 1 wherein the polycyclic polyene is selected from the group consisting of dicyclopentadiene, tricyclopentadiene and dimethanohexahydronaphalene.

5. An organosilicon prepolymer composition as claimed in claim 2 where the polycyclic polyene is selected from the group consisting of dicycloheptadiene, tricyclopentadiene and dimethanohexahydronaphthalene.

6. An organosilicon prepolymer composition as claimed in claim 1 wherein the ratio of carbon-carbon double bonds in the rings of (b) to ≡SiH groups in (a) is in the ratio of greater than 1.8 and up to 5:1.

7. An organosilicon prepolymer composition as claimed in claim 1 wherein the ratio of carbon-carbon double bonds in the rings of (b) to ≡SiH groups in (a) is in the ratio of greater than 1.8 and up to 2.2:1.

8. An organosilicon prepolymer composition as claimed in claim 5 wherein the ratio of carbon-carbon double bonds in the rings of (b) to ≡SiH groups in (a) is in the ratio of greater than 1.8:1 and up to about 2.2:1.

9. An organosilicon prepolymer composition as claimed in claim 2 wherein (a) is a cyclic polysiloxane having the general formula (I).

10. An organosilicon prepolymer composition as claimed in claim 8 wherein (a) is a cyclic polysiloxane having the general formula (I).

11. An organosilicon prepolymer composition as claimed in claim 2 wherein (a) is a tetrahedral siloxysilane having the general formula (II).

12. An organosilicon prepolymer composition as claimed in claim 8 wherein (a) is a tetrahedral siloxysilane having the general formula (II).

13. A low viscosity fluid comprising the organosilicon prepolymer composition of claim 1 and (c) at least one additional cyclic polysiloxane, additional tetrahedral siloxysilane or linear, short chain ≡SiH terminated polysiloxane, wherein the total ratio of carbon-carbon double bonds in the rings of (b) to ≡SiH groups in (a) and (c) is in the ratio of 0.4:1 to 1.7:1.

14. A low viscosity fluid comprising the organosilicon prepolymer composition of claim 8 and (c) at least one additional cyclic polysiloxane, additional tetrahedral siloxysilane or linear, short chain ≡SiH terminated polysiloxane, wherein the total ratio of carbon-carbon double bonds in the rings of (b) to ≡SiH groups in (a) and (c) is in the ratio of 0.4:1 to 1.7:1.

15. A low viscosity fluid as claimed in claim 14 wherein the linear, short chain ≡SiH terminated polysiloxane has the general formula:

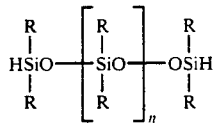

(III)

wherein n is 0 to 1000 and R is alkyl or aryl.

16. A low viscosity fluid as claimed in claim 15 wherein R is methyl or phenyl.

17. A low viscosity fluid as claimed in claim 14 wherein (c) contains 10 to 50%, by weight of (c), of the linear, short chain ≡SiH terminated polysiloxane.

18. A process for forming an organosilicon prepolymer composition comprising reacting, in the presence of a hydrosilation catalyst, (a) at least one cyclic polysiloxane or tetrahedral siloxysilane containing at least two ≡SiH groups and (b) at least one polycyclic polyene having at least two non-aromatic, non-conjugated carbon-carbon double bonds in its rings, wherein the total ratio of the non-aromatic, non-conjugated carbon-carbon double bonds in the rings of (b) to ≡SiH groups in (a) is at least 1.8:1 and either (a) or (b) has more than two reactive sites.

19. A process for forming an organosilicon crosslinked polymer, comprising curing the low viscosity fluid of claim 13 in the presence of a hydrosilation catalyst.

20. A process for forming an organosilicon crosslinked polymer, comprising curing the low viscosity fluid of claim 15 in the presence of a hydrosilation catalyst.

21. A process for forming an organosilicon crosslinked polymer, comprising:
(A) mixing the organosilicon prepolymer composition of claim 1 with (c) at least one additional cyclic polysiloxane, additional tetrahedral siloxysilane or linear, short chain ≡SiH terminated polysiloxane such that the total ratio of the non-aromatic, non-conjugated carbon-carbon double bonds in the rings of (b) to ≡SiH groups in (a) and (c) is in the range of 0.4:1 to 1.7:1; and
(B) curing the mixture in the presence of a hydrosilation catalyst.

22. A process for forming a fiber reinforced composite, comprising wetting fiber reinforcement with the low viscosity fluid of claim 13 and curing the fluid to form a crosslinked polymer in the presence of a hydrosilation catalyst.

23. A process for forming a fiber reinforced composite, comprising wetting fiber reinforcement with the low viscosity fluid of claim 15 and curing the fluid to form a crosslinked polymer in the presence of a hydrosilation catalyst.

24. A process for forming a fiber reinforced composite, comprising:
(A) forming a low-viscosity fluid blend by mixing the organosilicon prepolymer composition of claim 1 with (c) at least one additional cyclic polysiloxane, additional tetrahedral siloxysilane or linear, short chain ≡SiH terminated polysiloxane such that the total ratio of the non-aromatic, non-conjugated carbon-carbon double bonds in the rings of (b) to ≡SiH groups in (a) and (c) is in the range of greater than 0.4:1 and up to 1.7:1;
(B) injecting the mixture into a mold containing fiber reinforcement; and
(C) curing the mixture in the presence of a hydrosilation catalyst so as to form a fiber reinforced composite.

* * * * *

UNITED STATES PATENT AND TRADEMARK OFFICE
CERTIFICATE OF CORRECTION

PATENT NO. : 5,013,809                                Page 1 of 2

DATED     : May 7, 1991

INVENTOR(S) : Raymond T. Leibfried, Sr.

It is certified that error appears in the above-identified patent and that said Letters Patent is hereby corrected as shown below:

Title Page:
Abstract, line 8, directly after (a), delete "in" and replace it with --is--.

Col. 1, line 64, delete "non" and replace it with --non- --.

Col. 1, line 65, delete "non-conJugated" and replace it with --non-conjugated--.

Col. 3, line 35, delete "platinum containing" and replace it with --platinum-containing--.

Col. 3, line 37, directly after "($H_2PtCl_6 \cdot 6H_2O$)", insert a --.--.

Col. 4, line 22, directly after "reaction", insert --can--.

Col. 4, line 26, delete "ar" and replace it with --are--.

Col. 4, line 41, delete the space directly after the slash.

Col. 6, line 62, delete "1/4 inch" and replace it with --1/2 inch--.

Col. 7, line 17, delete "Prepared" and replace it with --prepared--.

UNITED STATES PATENT AND TRADEMARK OFFICE
CERTIFICATE OF CORRECTION

PATENT NO. : 5,013,809
DATED : May 7, 1991
INVENTOR(S) : Raymond T. Leibfried, Sr.

It is certified that error appears in the above-identified patent and that said Letters Patent is hereby corrected as shown below:

Claim 4, col. 12, line 23, delete "phalene" and replace it with --phthalene--.

Signed and Sealed this

Eighth Day of December, 1992

*Attest:*

DOUGLAS B. COMER

*Attesting Officer*      *Acting Commissioner of Patents and Trademarks*

UNITED STATES PATENT AND TRADEMARK OFFICE
CERTIFICATE OF CORRECTION

PATENT NO. : 5,013,809
DATED : May 7, 1991
INVENTOR(S) : Raymond T. Leibfried, Sr.

It is certified that error appears in the above-identified patent and that said Letters Patent is hereby corrected as shown below:

Col. 3, lines 10-16

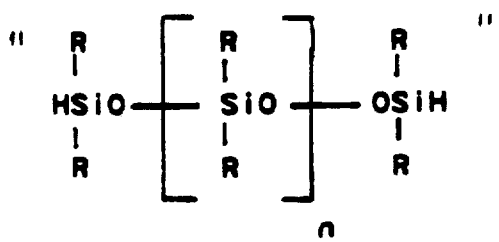 Should read 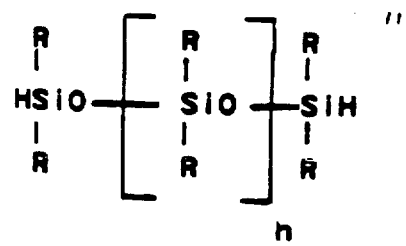

In the claims, Col. 13, between lines 1 and 7

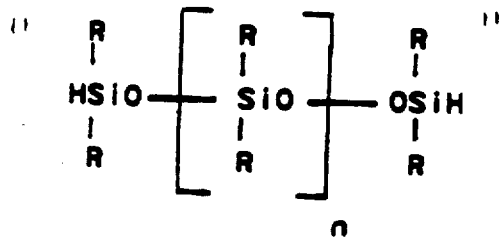 Should read 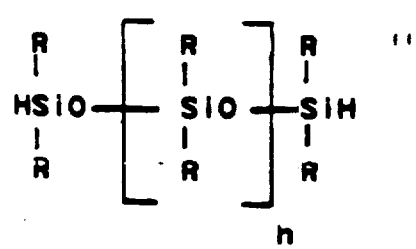

Signed and Sealed this

Twenty-second Day of June, 1993

Attest:

MICHAEL K. KIRK

Attesting Officer     Acting Commissioner of Patents and Trademarks